(12) United States Patent
Suzuki et al.

(10) Patent No.: US 9,818,177 B2
(45) Date of Patent: Nov. 14, 2017

(54) IMAGE PROCESSING APPARATUS, IMAGE PROCESSING METHOD, AND COMPUTER-READABLE RECORDING MEDIUM

(71) Applicant: FUJITSU FRONTECH LIMITED, Tokyo (JP)

(72) Inventors: Tomoharu Suzuki, Tokyo (JP); Shinichi Eguchi, Tokyo (JP)

(73) Assignee: Fujitsu Frontech Limited, Tokyo (JP)

( * ) Notice: Subject to any disclaimer, the term of this patent is extended or adjusted under 35 U.S.C. 154(b) by 78 days.

(21) Appl. No.: 14/847,594

(22) Filed: Sep. 8, 2015

(65) Prior Publication Data

US 2015/0379696 A1 Dec. 31, 2015

Related U.S. Application Data

(63) Continuation of application No. PCT/JP2014/056496, filed on Mar. 12, 2014.

(30) Foreign Application Priority Data

Mar. 13, 2013 (JP) ................................ 2013-051008

(51) Int. Cl.
*G06T 5/00* (2006.01)
*G06T 3/40* (2006.01)
(Continued)

(52) U.S. Cl.
CPC .............. *G06T 5/002* (2013.01); *A61B 5/117* (2013.01); *A61B 5/1171* (2016.02);
(Continued)

(58) Field of Classification Search
None
See application file for complete search history.

(56) References Cited

U.S. PATENT DOCUMENTS 9,245,168 B2 1/2016 Suzuki et al.
2003/0123584 A1 7/2003 Siegel et al.
(Continued)

FOREIGN PATENT DOCUMENTS

JP 2008-015741 A 1/2008
JP 2010-211757 9/2010
(Continued)

OTHER PUBLICATIONS

Alleysson, D.—"Color demosaicing by estimating luminance and opponent chromatic signals in the Fourier domain"—2002, pp. 1-6.*

(Continued)

*Primary Examiner* — Bernard Krasnic
(74) *Attorney, Agent, or Firm* — Greer Burns & Crain Ltd.

(57) ABSTRACT

The image processing apparatus is configured by including a palm luminance estimation unit and a surface reflected component enhancement unit that separate low-frequency components from a signal indicating luminance values of pixels of an input image, a denoising processing unit that executes a denoising process for the signal from which the low-frequency components have been separated, and a merging unit that generates an image by merging the signal after the denoising process and the low-frequency components.

3 Claims, 23 Drawing Sheets

(51) Int. Cl.
  *A61B 5/1171* (2016.01)
  *A61B 5/117* (2016.01)
  *G06K 9/00* (2006.01)
  *G06K 9/46* (2006.01)
  *G06T 11/00* (2006.01)
  *G06T 11/60* (2006.01)
  *A61B 5/00* (2006.01)

(52) U.S. Cl.
  CPC ....... *G06K 9/00033* (2013.01); *G06K 9/4609* (2013.01); *G06T 3/4015* (2013.01); *G06T 5/008* (2013.01); *G06T 11/001* (2013.01); *G06T 11/60* (2013.01); *A61B 5/0077* (2013.01); *A61B 5/0086* (2013.01); *A61B 5/489* (2013.01); *A61B 2576/00* (2013.01); *G06K 2009/00932* (2013.01); *G06T 2207/10024* (2013.01); *H04N 2209/046* (2013.01)

(56) References Cited

U.S. PATENT DOCUMENTS

| | | | |
|---|---|---|---|
| 2004/0044531 | A1 | 3/2004 | Kasabov et al. |
| 2008/0122953 | A1 | 5/2008 | Wakahara et al. |
| 2009/0021611 | A1 | 1/2009 | Utsugi |
| 2011/0176730 | A1 | 7/2011 | Sasaki |
| 2013/0033578 | A1* | 2/2013 | Wajs ............... G06T 7/0065 348/46 |
| 2013/0033579 | A1* | 2/2013 | Wajs ............... G02B 7/365 348/46 |
| 2013/0071024 | A1 | 3/2013 | Jang et al. |
| 2013/0089268 | A1 | 4/2013 | Nguyen et al. |
| 2013/0113988 | A1* | 5/2013 | Wajs ............... H04N 5/225 348/362 |

FOREIGN PATENT DOCUMENTS

| | | |
|---|---|---|
| JP | 2011-035893 | 2/2011 |
| JP | 2011-143100 | 7/2011 |
| WO | WO 2012/007049 A1 | 1/2012 |
| WO | WO 2012/111664 A1 | 8/2012 |
| WO | WO 2012/144158 A1 | 10/2012 |

OTHER PUBLICATIONS

Extended EP Search Report dated Oct. 12, 2016.
Alleysson et al.; "Linear Demosaicing Inspired by the Human Visual System"; IEEE Trans. on Image Processing, IEEE Service Center; Piscataway, NJ; vol. 14, No. 4; Apr. 1, 2005; pp. 439-449.
Adams et al.; "Digital Camera Image Processing Chain Design" In: "Single-Sensor Imaging: Methods and Applications for Digital Cameras"; CRC Press; Sep. 9, 2008; pp. 67-103.
Ruikar et al.; "Wavelet Based Image Denoising Technique"; International Journal of Advanced Computer Science and Applications; Mar. 1, 2011; pp. 49-53; http://ijacsa.thesai.org/.
Notice of Rejection Grounds dated Oct. 25, 2016 in co-pending Japanese Patent App. No. 2015-505516 (with English machine translation).
Int'l. Search Report issued in Int'l. App. No. PCT/JP2014/056496, dated Jun. 24, 2014.
Written Opinion of Int'l. Searching Authority for Int'l. App. No. PCT/JP2014/056496, dated Jun. 10, 2014 (with partial translation).
Notice of rejection Grounds issued in corresponding Japanese App. No. 2015-505516, dated Jul. 4, 2016 (with English translation).
Office action issued in corresponding U.S. Appl. No. 15/464,989, dated May 1, 2017.

* cited by examiner

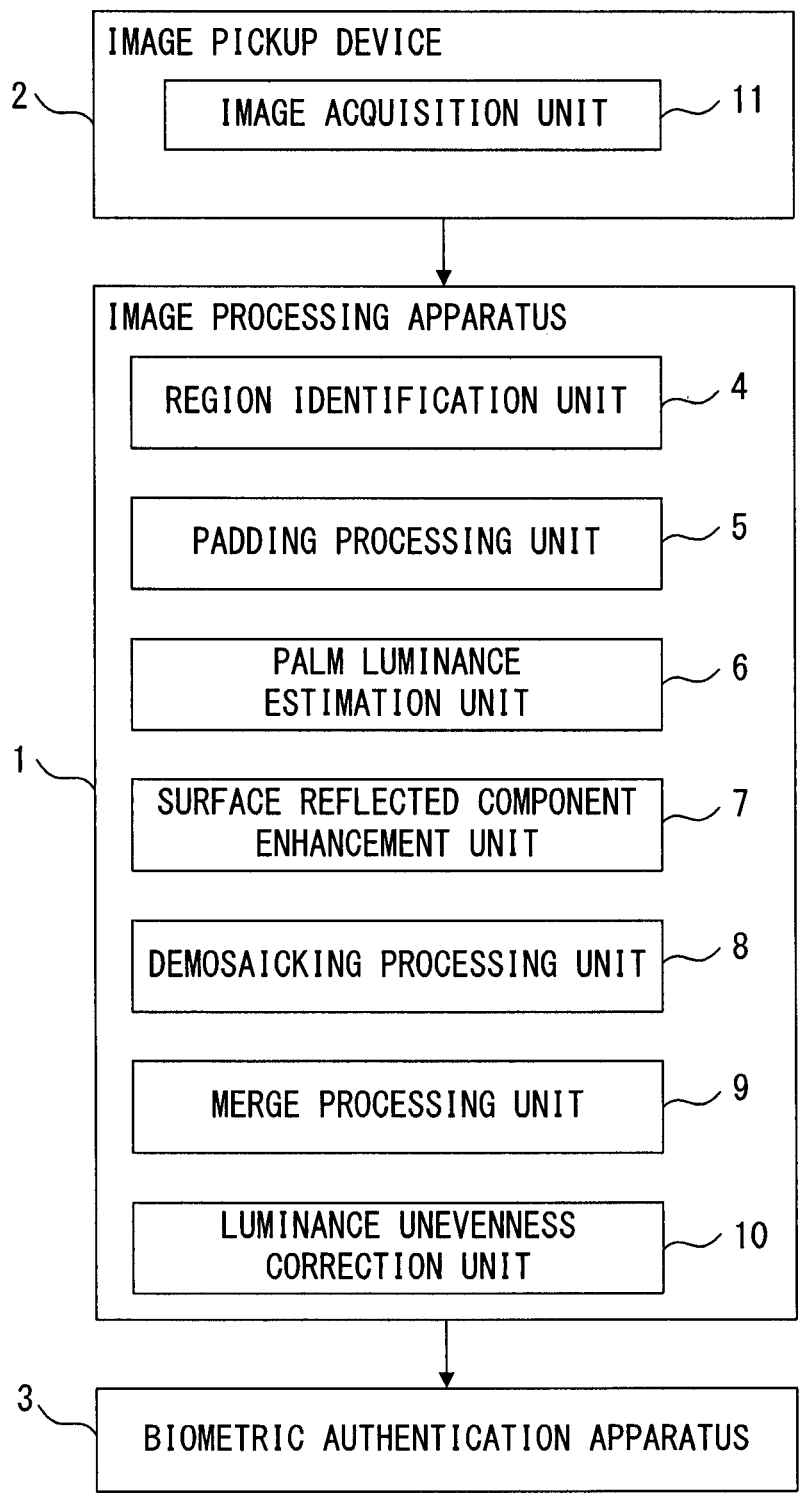
F I G. 1

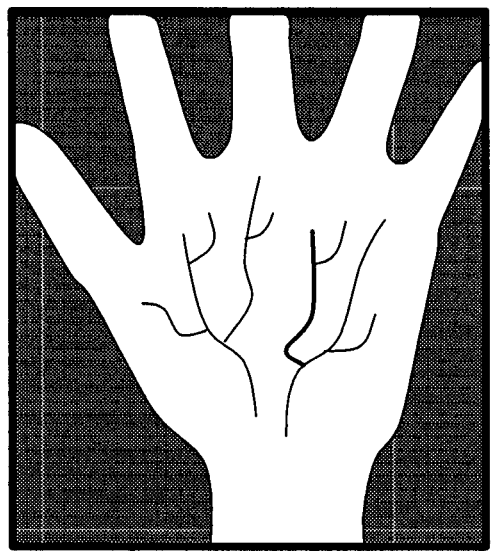
F I G. 3

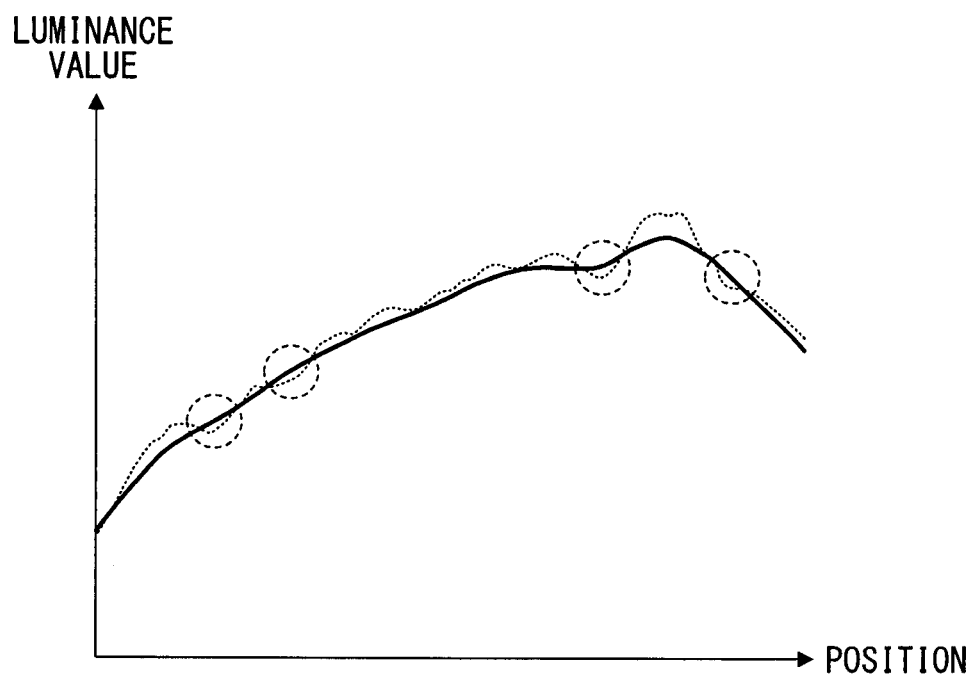
F I G. 8

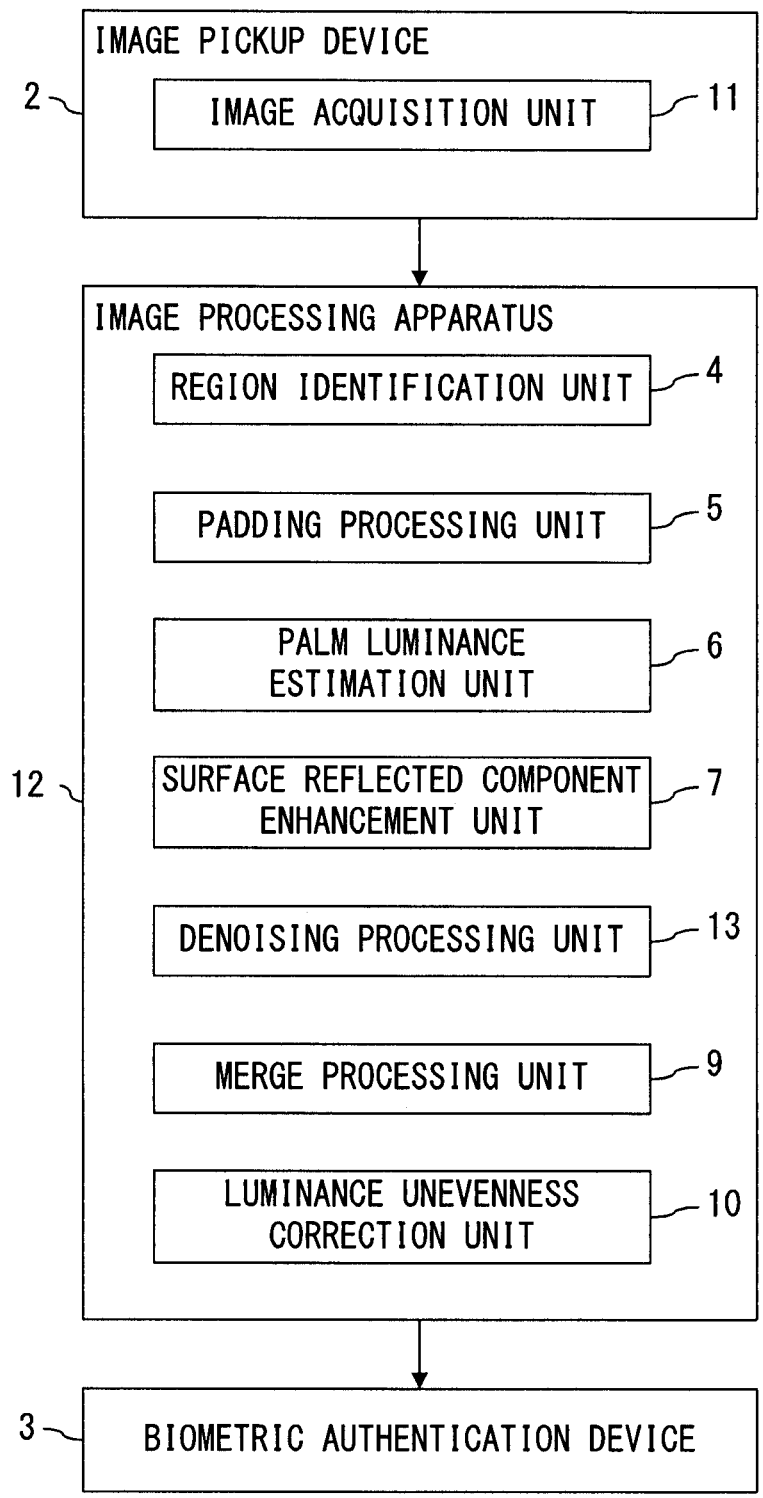
F I G. 1 2

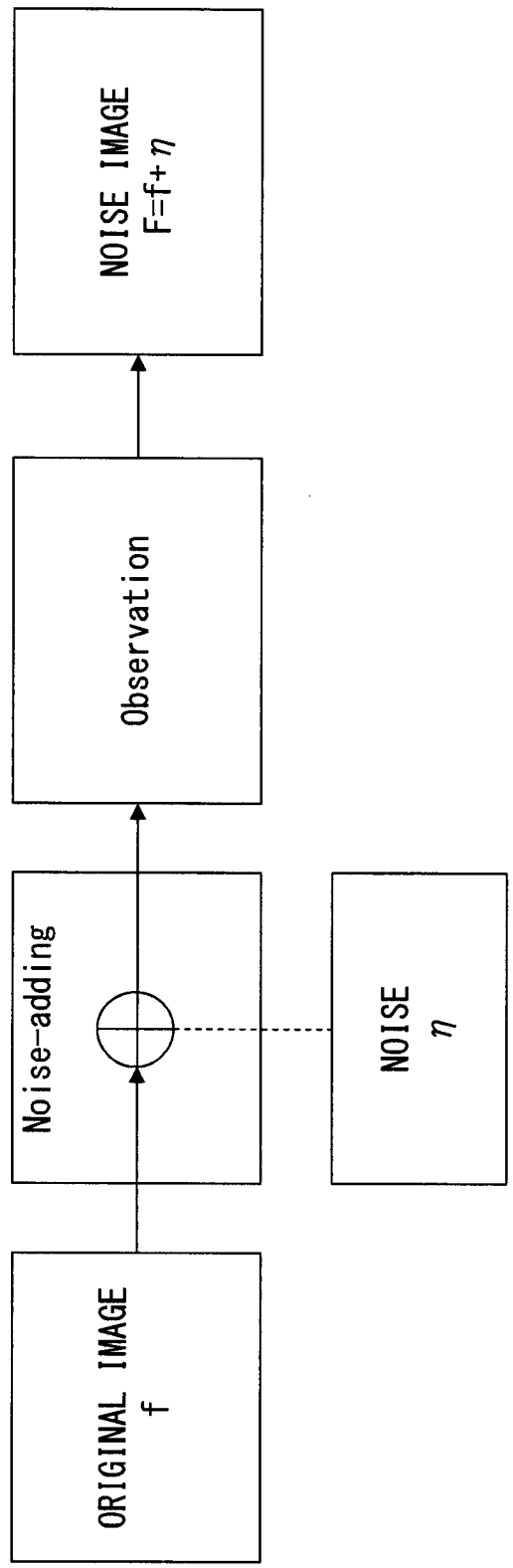
F I G. 14

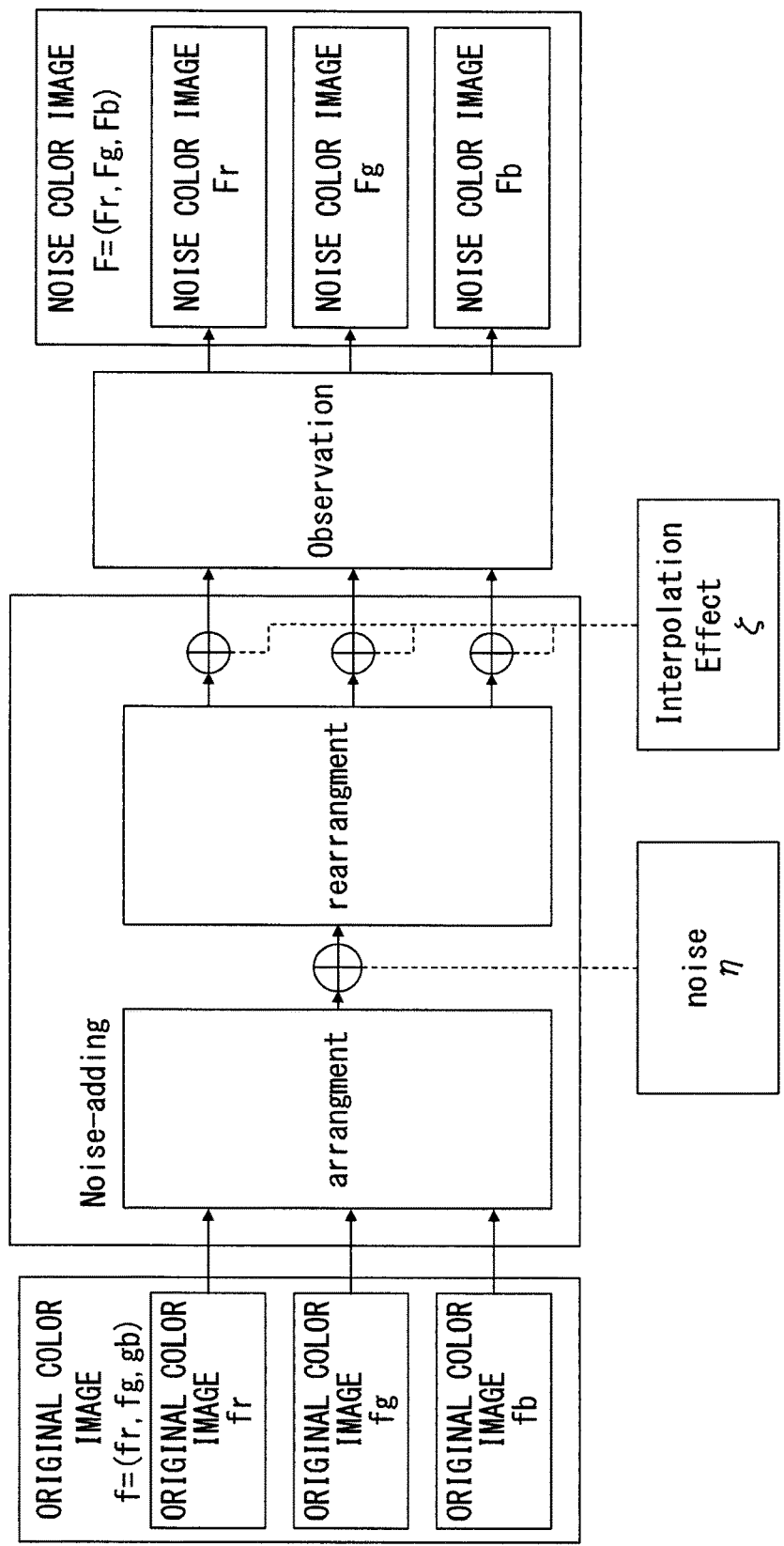
F I G. 15

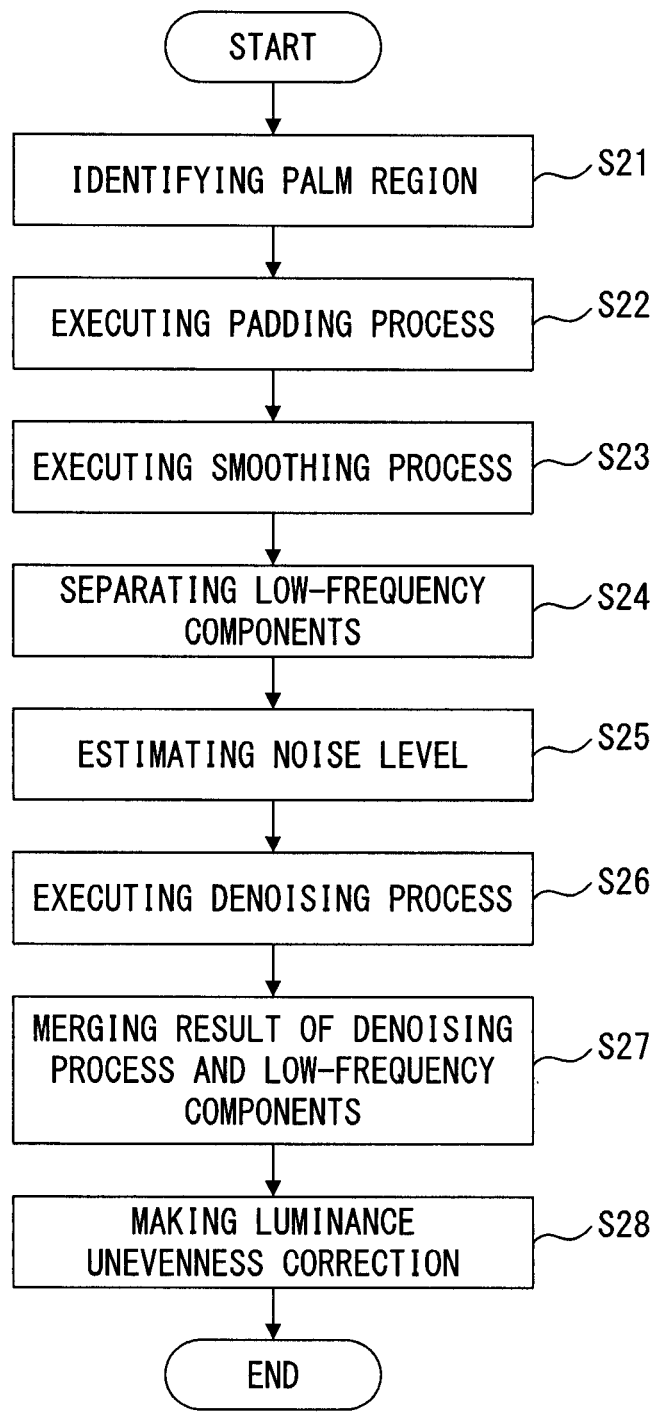
F I G. 1 8

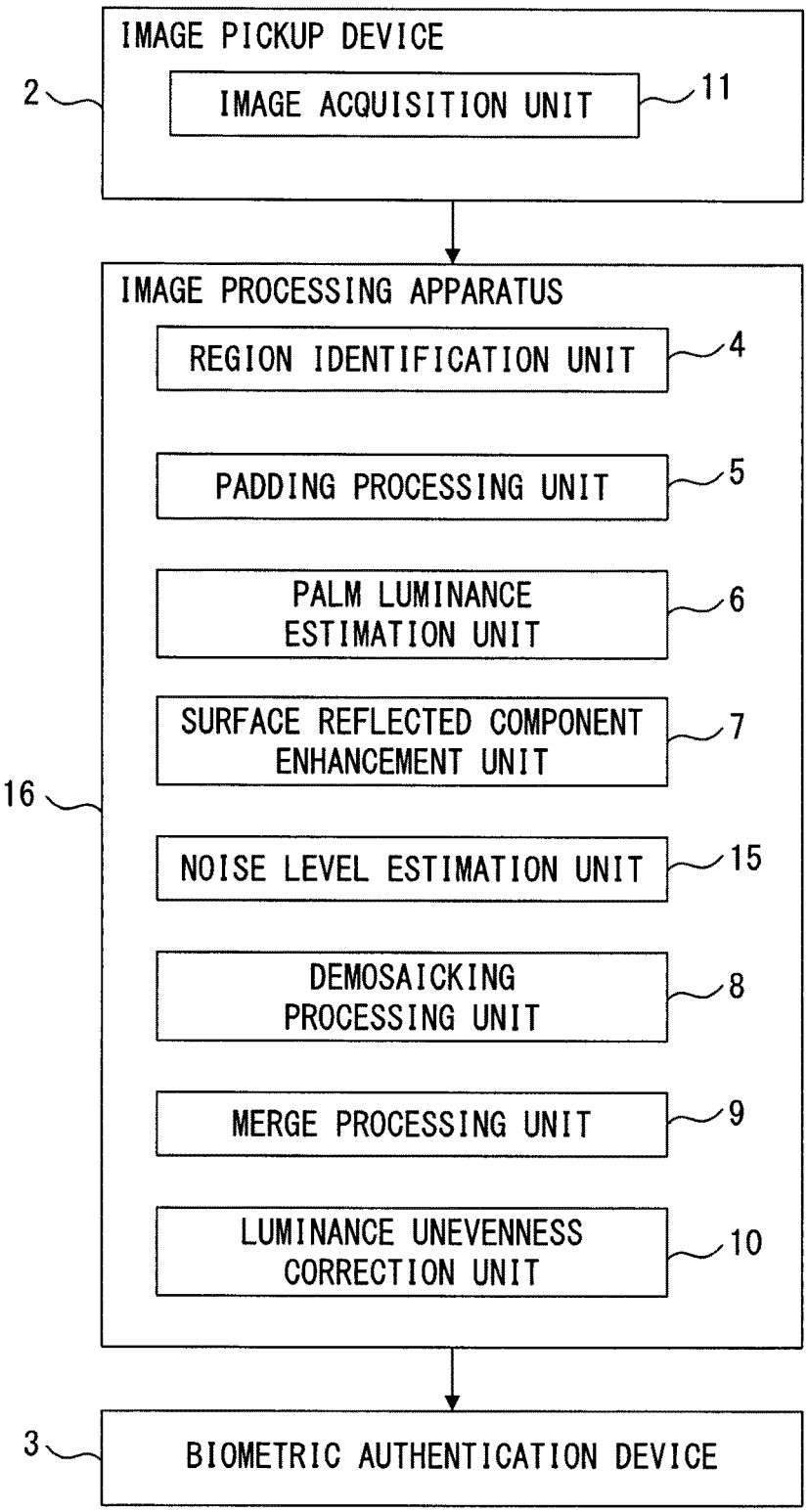
F I G. 20

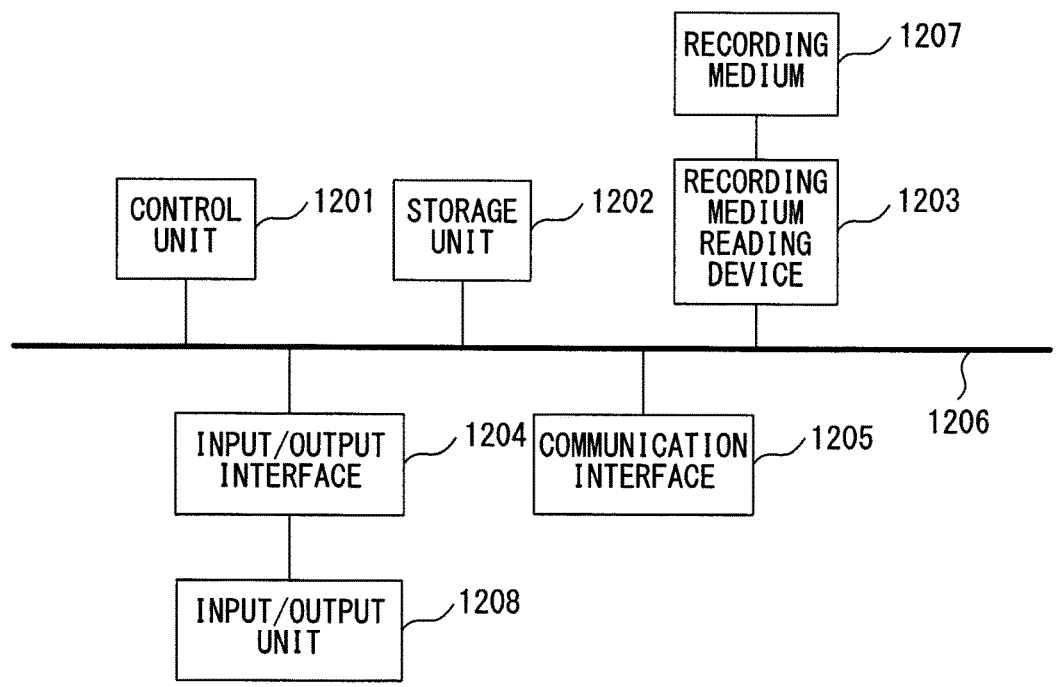
F I G. 2 3

IMAGE PROCESSING APPARATUS, IMAGE PROCESSING METHOD, AND COMPUTER-READABLE RECORDING MEDIUM

CROSS-REFERENCE TO RELATED APPLICATIONS

This application is a continuation application of International Application PCT/JP2014/056496 filed on Mar. 12, 2014, designating the U.S. and claiming priority to Japan 2013/051008, filed on Mar. 13, 2013. The entire contents of both applications are incorporated herein by reference.

FIELD

The present invention relates to a technique of executing an image process for an image including biological information.

BACKGROUND

An existing biometric authentication device executes a biometric authentication process by picking up an image of a subject with the use of a dedicated image pickup device such as an infrared camera or the like, and by determining whether biological information extracted from the picked-up image and preregistered biological information match.

Incidentally, biometric authentication devices provided with a general-purpose image pickup device are expected to command a large market share hereafter due to the recent trend of decreasing prices for biometric authentication devices. For example, as a general-purpose image pickup device, an image pickup device provided with a single-chip image pickup element, RGB color filters of a Bayer arrangement, and the like is conceivable. Moreover, a demosaicking process is executed for a signal indicating luminance values of pixels of an image picked up by such an image pickup device so as to reduce a sampling noise caused by a difference among frequency bands of light rays that pass through the color filters, an imbalance among light absorption characteristics of the color filters, or the like (for example, see Japanese Laid-open Patent Publication No. 2011-143100).

Additionally, shapes of veins are sometime used as biological information for biometric authentication. In this case, a luminance value of a portion that exhibits the veins in a picked-up image is smaller than that of a portion peripheral to the veins due to the light absorption characteristic of reduced hemoglobin within blood, and a change in the luminance value is smaller than that in the portion peripheral to the veins. Accordingly, when a demosaicking process is executed for an image including the veins, low-frequency components can be possibly reduced along with a sampling noise, leading to a possible difficulty in extracting the shapes of the veins as biological information from the image for which the demosaicking process has been executed.

SUMMARY

An image processing apparatus according to the present invention includes: a separation unit that separates low-frequency components from a signal indicating luminance values of pixels of an input image; a demosaicking processing unit that executes a demosaicking process for the signal from which the low-frequency components have been separated; and a merging unit that generates an image by merging the signal after the demosaicking process and the low-frequency components.

Additionally, an image processing method according to the present invention includes: separating, by a computer, low-frequency components from a signal indicating luminance values of pixels of an input image; executing, by the computer, a demosaicking process for the signal from which the low-frequency components have been separated; and generating, by the computer, an image by merging the signal after the demosaicking process and the low-frequency components.

Furthermore, a program according to the present invention causes a computer to execute a process including: separating low-frequency components from a signal indicating luminance values of pixels of an input image; executing a demosaicking process for the signal from which the low-frequency components have been separated; and generating an image by merging the signal after the demosaicking process and the low-frequency components.

Still further, an image processing apparatus according to the present invention includes: a separation unit that separates low-frequency components from a signal indicating luminance values of pixels of an input image; a denoising processing unit that executes a denoising process for the signal from which the low-frequency components have been separated; and a merging unit that generates an image by merging the signal after the denoising process and the low-frequency components.

Still further, an image processing method according to the present invention includes: separating, by a computer, low-frequency components from a signal indicating luminance values of pixels of an input image; executing, by the computer, a denoising process for the signal from which the low-frequency components have been separated; and generating, by the computer, an image by merging the signal after the denoising process and the low-frequency components.

Still further, a program according to the present invention causes a computer to execute a process including: separating low-frequency components from a signal indicating luminance values of pixels of an input image; executing a denoising process for the signal from which the low-frequency components have been separated; and generating an image by merging the signal after the denoising process and the low-frequency components.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 illustrates an example of an image processing apparatus according to an embodiment;

FIG. 3 illustrates an example of an image input to the image processing apparatus;

FIG. 8 illustrates results "fσ(i,j)" and "Iest" obtained by performing a convolution operation between "f(i,j)" and a Gaussian function;

FIG. 12 illustrates an example of an image processing apparatus according to a different embodiment;

FIG. 14 illustrates an example of an observation model of a noise image;

FIG. 15 illustrates an example of an observation model of a noise image related to a demosaicking process;

FIG. 18 is a flowchart illustrating operations of the image processing apparatus;

FIG. 20 illustrates an image processing apparatus according to a further different embodiment;

FIG. 23 illustrates an example of hardware of the image processing apparatus.

DESCRIPTION OF EMBODIMENTS

Figure 2:
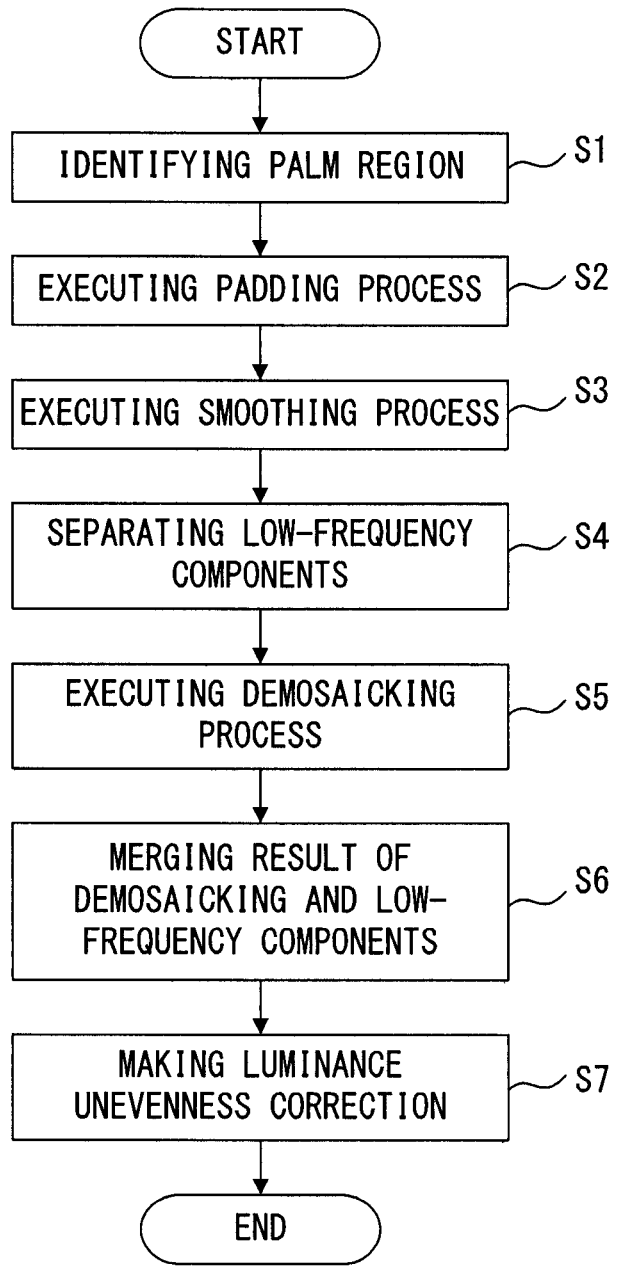
FIG. 2 is a flowchart illustrating operations of the image processing apparatus.

FIG. 1 illustrates an image processing apparatus according to an embodiment.

The image processing apparatus 1 illustrated in FIG. 1 executes an image process such as a demosaicking process or the like for an image picked up by an image pickup device 2, and outputs the image to the biometric authentication device 3. The image processing apparatus 1 includes a region identification unit 4, a padding processing unit 5, a palm luminance estimation unit 6 (separation unit), a surface reflected component enhancement unit 7 (separation unit), a demosaicking processing unit 8, a merge processing unit 9 (merging unit), and a luminance unevenness correction unit 10.

The image pickup device 2 includes an image acquisition unit 11 that obtains a picked-up image of a subject by using a single-chip image pickup element, and RGB color filters of a Bayer arrangement.

The biometric authentication device 3 executes a biometric authentication process by extracting biological information (such as shapes of veins) from an image for which an image process has been executed by the image processing apparatus 1, and by determining whether the extracted biological information and preregistered biological information match.

The image for which the image process has been executed by the image processing apparatus 1 may be used as information for determining whether a subject is a living body, or as a medical image.

FIG. 2 is a flowchart illustrating operations of the image processing apparatus 1.

Figure 4:
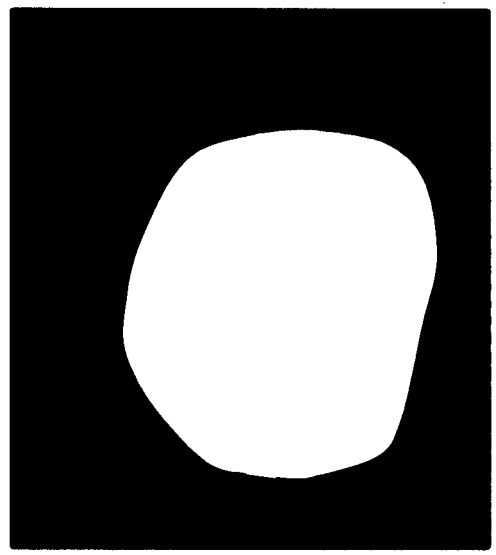
FIG. 4 illustrates an example of a result obtained by identifying a palm region.

When an image obtained by the image acquisition unit 11 is input, the region identification unit 4 initially identifies a "palm region", which is a region equivalent to the palm of a subject in the image (S1). For example, when the image obtained by picking up the palm illustrated in FIG. 3 is input, the region identification unit 4 whitens pixels corresponding to the "palm region" ("mask(i,j):=1") among pixels of the input image, and blackens pixels corresponding to a region other than the "palm region" ("mask(i,j):=0") as illustrated in FIG. 4 in accordance with the definition represented by the following formula 1. Note that "i" indicates a position in a horizontal axis direction of two-dimensional coordinates when a position of each pixel of the image input to the region identification unit 4 is made to correspond to the position in the two-dimensional coordinates, and "j" indicates the position of each pixel in a vertical axis direction of the two-dimensional coordinates. Moreover, "mask (i,j)" indicates a luminance value of a pixel at an arbitrary position (i,j) among the pixels of the image input to the region identification unit 4. Additionally, "ROI (Region Of Interest)" indicates the "palm region". An algorithm for setting the ROI is not particularly limited.

$$\mathrm{mask}(i, j) := \begin{cases} 1 & ((i, j) \in ROI) \\ 0 & ((i, j) \notin ROI) \end{cases} \quad \text{formula 1}$$

Figure 5:
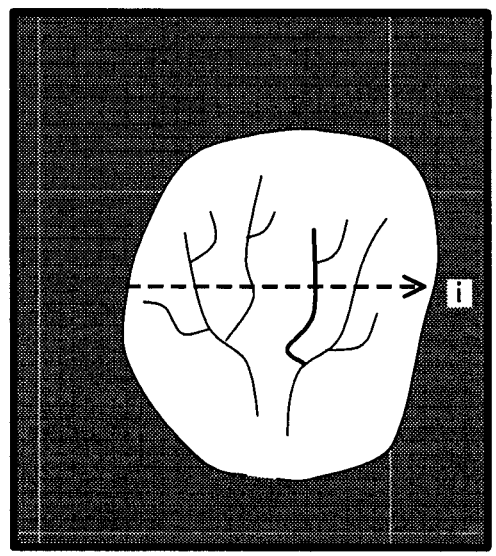
FIG. 5 illustrates an example of a result obtained by executing a padding process.

Next, the padding processing unit 5 executes a padding process by setting luminance values of corresponding pixels among the pixels of the image input in S1 as luminance values of the pixels of the "palm region", and by setting an average value of the luminance values set for the pixels of the "palm region" as luminance values of pixels of the region other than the "palm region" (S2). For example, the padding processing unit 5 sets a luminance value "f(i,j) (if mask(i,j)=1)" of a corresponding pixel among the pixels of the image input in S1 as a luminance value "fmp(i,j)" of the pixels of the "palm region", and sets an average value "μ" of the luminance values set for the pixels of the "palm region" as the luminance value "fmp(i,j)" of the pixels of the region other than the "palm region", as illustrated in FIG. 5 in accordance with the definition represented by the following formula 2.

$$fmp(i, j) := \begin{cases} f(i, j) & (\text{if } \mathrm{mask}(i, j) = 1) \\ \mu & (\text{if } \mathrm{mask}(i, j) = 0) \end{cases} \quad \text{formula 2}$$

Figure 6:
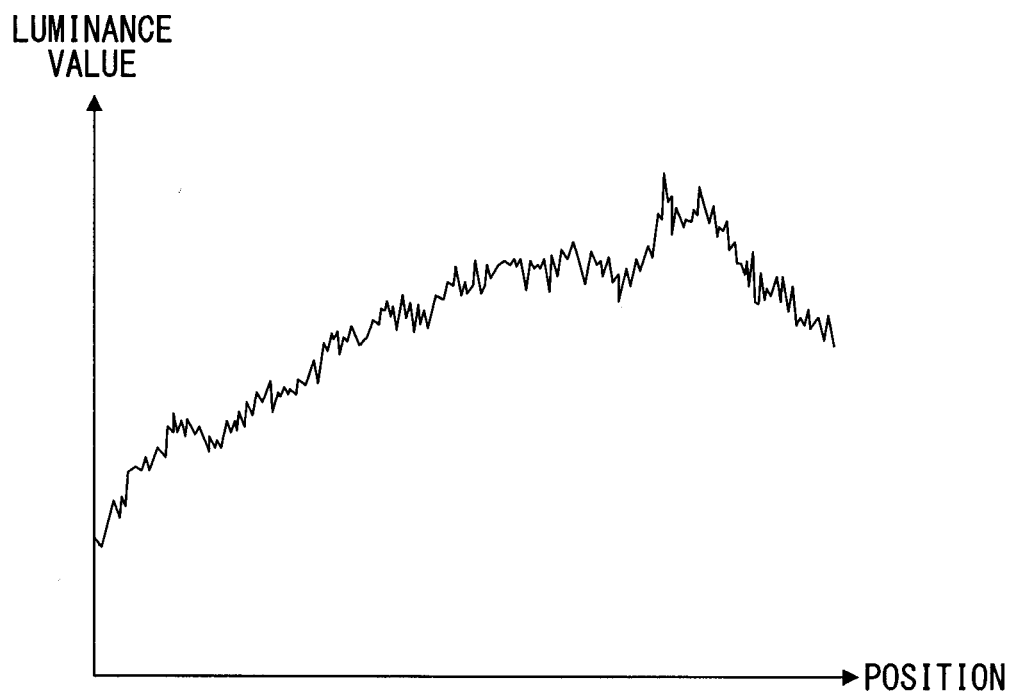
FIG. 6 illustrates an example of a signal that indicates luminance values of pixels corresponding to one line in the palm region.
Figure 7:
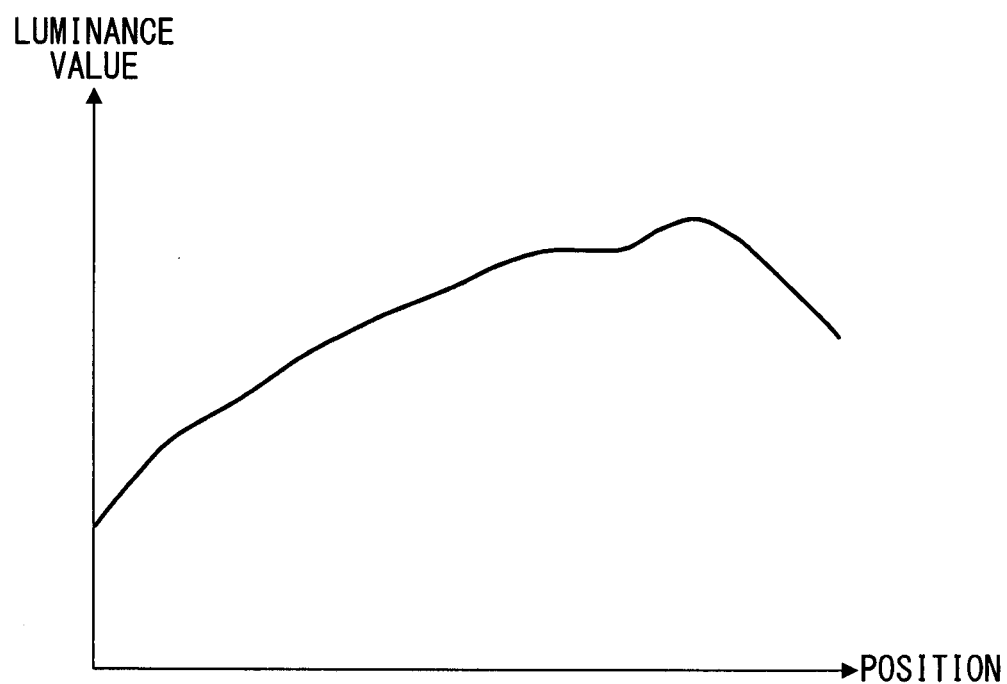
FIG. 7 illustrates an example of a result "Iest(i,j)" obtained by executing a smoothing process for "f(i,j)"

Next, the palm luminance estimation unit 6 estimates a signal indicating luminance values of pixels of the "palm region" in which high-frequency components (a signal indicating a luminance value that significantly changes, such as a luminance value indicating light reflected on the surface of the palm, or the like) and low-frequency components (a signal indicating a luminance value that moderately changes, such as a luminance value indicating light reflected on a vein, or the like) are reduced, by executing a smoothing process for the signal indicating the luminance values of pixels of the "palm region" set in S2 (S3). For example, the palm luminance estimation unit 6 estimates a signal "Iest" indicating the luminance values of pixels of the "palm region" in which high-frequency components and low-frequency components are reduced in accordance with the definition represented by the following formula 3 by executing the smoothing process such as a smoothing-spline conversion process or the like for the signal "fmp" that indicates the luminance values of pixels of the "palm region" set in S2. FIG. 6 illustrates an example of a signal indicating luminance values of pixels corresponding to one (dashed line) in an i-axis direction of the "palm region" illustrated in FIG. 5. A horizontal axis of the graph illustrated in FIG. 6 indicates a position in the i-axis direction of the "palm region" illustrated in FIG. 5, while the vertical axis indicates a luminance value. FIG. 7 illustrates a result obtained by executing the smoothing-spline conversion process for the luminance values of pixels illustrated in FIG. 6. Moreover, the smoothing process executed by the palm luminance estimation unit 6 is not particularly limited as long as it can reduce high-frequency components and low-frequency components for the luminance values of pixels of the "palm region" set in S2.

$$\text{Iest}:=\text{IntensityEstimation}(fmp) \qquad \text{formula 3}$$

Figure 9:
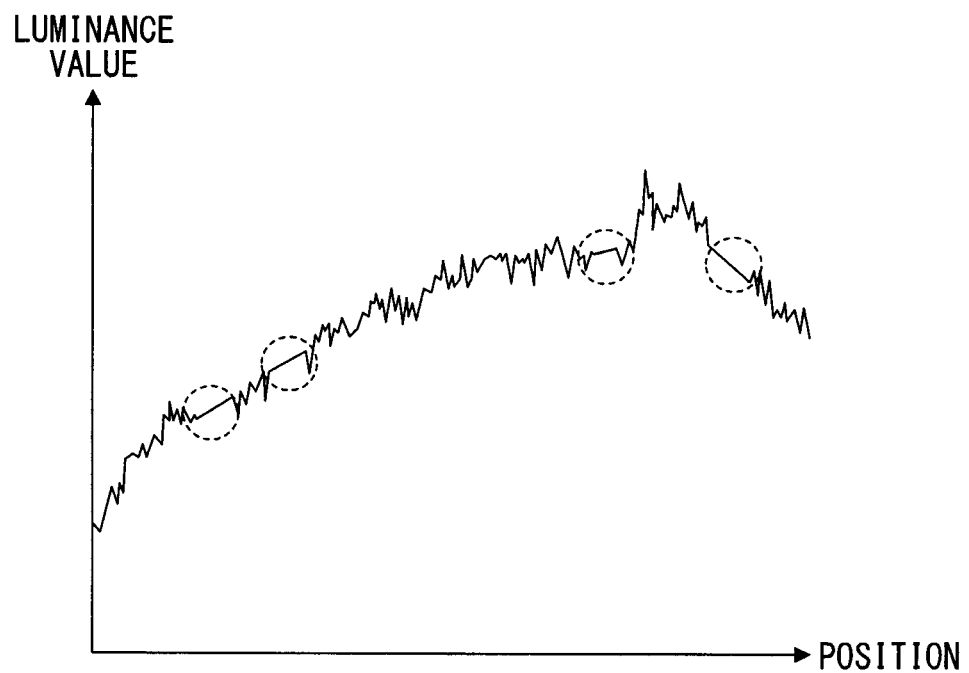
FIG. 9 illustrates an example of a result "fspec(i,j)" obtained by separating low-frequency components from "f(i,j)".

Then, the surface reflected component enhancement unit 7 separates low-frequency components from the signal indicating the luminance values of pixels of the "palm region" set in S2 by using the signal indicating the luminance values of pixels for which the smoothing process has been executed in S3 (S4). For example, when a result "fσ(i,j)" (dotted line illustrated in FIG. 8) obtained by executing a convolution operation process between "f(i,j)" and a "Gaussian function g(i,j)" in accordance with the definition represented by the following formula 4 is equal to or larger than "Iest−d" (solid line illustrated in FIG. 8), the surface reflected component enhancement unit 7 sets "f(i,j)" as the luminance value "fspec(i,j)" of pixels of the "palm region" after the low-frequency components have been separated as illustrated in FIG. 9, and sets the luminance value "Iest(i,j)" (within dashed line circles illustrated in FIG. 9) of pixels for which the smoothing process has been executed in S3 as "fspec(i,j)" as illustrated in FIG. 9 when "fσ(i,j)" is smaller than "Iest−d" (within dashed line circles illustrated in FIG. 8). At this time, the surface reflected component enhancement unit 7 determines that "fσ(i,j)", which is smaller than "Iest−d", is a low-frequency component of the signal indicating the luminance values of pixels of the "palm region" set in S2. "d" is assumed to be a positive integer that is smaller than the amplitude of a low-frequency component, and is set to offset, toward the bottom side of the graph illustrated in FIG. 8, the signal "Iest" indicating the luminance values of pixels for which the smoothing process has been executed in S3. In the signal indicating the luminance values of pixels of the "palm region", the number of low-frequency components is smaller than that of high-frequency components, and "Iest" is shifted toward the side of the region including high-frequency components (toward the top side of the graph illustrated in FIG. 8) by being affected due to the fact that the number of low-frequency components is smaller. In this embodiment, the low-frequency components are separated with higher accuracy from the luminance values of pixels of the "palm region" set in S2 by offsetting "Iest" toward the bottom side of the graph illustrated in FIG. 8. Moreover, "d" may be set to 0. Additionally, the convolution operation process executed by the surface reflected component enhancement unit 7 is not particularly limited as long as it can reduce a sampling noise or the like while a trend for high-frequency components and low-frequency components is being preserved for "f(i,j)".

$$fspec(i, j) := \begin{cases} f(i, j) & (\text{if } f\sigma(i, j)) \geq Iest - d \\ Iest(i, j) & (\text{if } f\sigma(i, j)) < Iest - d \end{cases} \qquad \text{formula 4}$$

Note that the surface reflected component enhancement unit 7 may be configured to set, in accordance with the definition represented by the following formula 5, a bigger value of the maximum value of "fmp" and the maximum value of "Iest" as the signal "fspec" indicating the luminance values of pixels of the "palm region" after the low-frequency components have been separated.

$$fspec:=\max(fmp,\text{Iest}) \qquad \text{formula 5}$$

Figure 10:
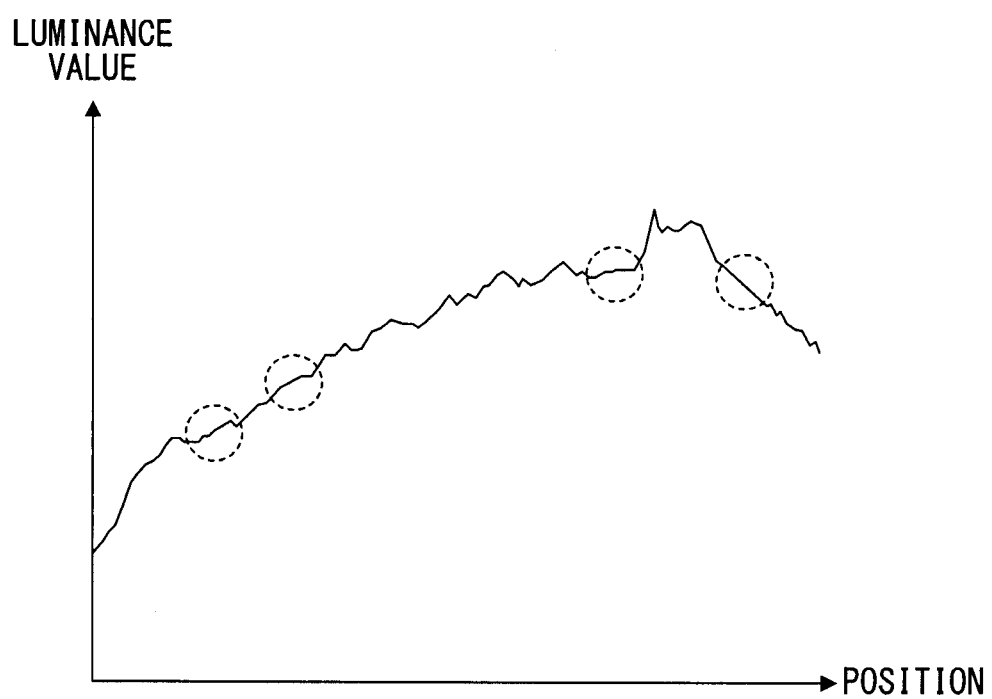
FIG. 10 illustrates an example of a result "fdemos(i,j)" obtained by executing a demosaicking process for "fspec (i,j)"

Next, the demosaicking processing unit 8 executes the demosaicking process for the signal indicating the luminance values of pixels of the "palm region" from which the low-frequency components have been separated in S4 (S5). For example, the demosaicking processing unit 8 executes, in accordance with the following formula 6, the demosaicking process for the signal "fspec" indicating the luminance values of pixels of the "palm region" from which the low-frequency components have been separated in S4. FIG. 10 illustrates a result "fdemos" for which the demosaicking process has been executed for the signal "fspec" indicating the luminance values of pixels by 1 line after the low-frequency components illustrated in FIG. 9 have been separated. Note that the demosaicking processing unit 8 may also be configured to execute a denoising process when it executes the demosaicking process. Moreover, an algorithm of the demosaicking process executed by the demosaicking processing unit 8 is not particularly limited as long as it can reduce a sampling noise while a trend for high-frequency components is preserved for "fspec".

$$fdemos:=\text{demosaicking}(fspec) \qquad \text{formula 6}$$

Figure 11:
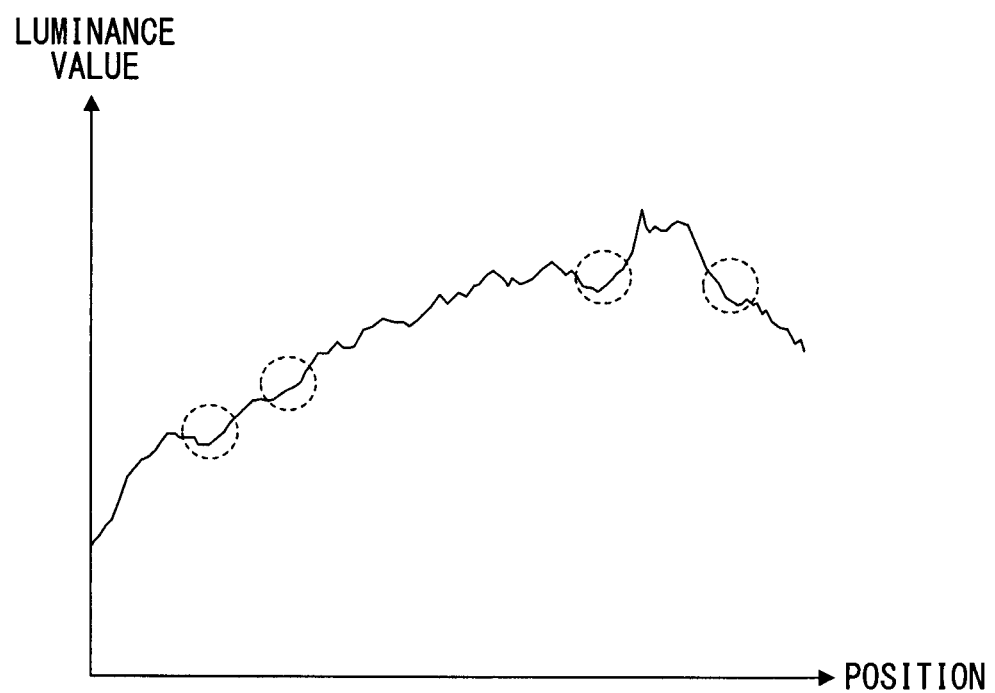
FIG. 11 illustrates an example of a merging result "fmerge (i,j)" between "fdemos_gray(i,j)" and (fσ(i,j)"

Next, the merge processing unit 9 merges the signal indicating the luminance values of pixels of the "palm region" for which the demosaicking process has been executed in S5 and the low-frequency components separated in S4 (S6). For example, when "fσ(i,j)" is equal to or larger than "Iest−d" in accordance with the definition represented by the following formula 7, the merge processing unit 9 sets, as the luminance value "fmerge(i,j)" of pixels of the "palm region" after being merged, the luminance value "fdemos_gray(i,j) (a solid line outside the dashed line circles illustrated in FIG. 11) obtained after a grayscale conversion process has been executed for the luminance value "fdemos(i,j)" of pixels obtained after the demosaicking process has been executed in S5, and sets, as "fmerge(i,j)", "fσ(i,j)" (the solid line within the dashed line circles illustrated in FIG. 11) when "fσ(i,j)" is smaller than "Iest−d". Note that an algorithm of the grayscale conversion is not particularly limited.

$$fmerge(i, j) := \begin{cases} fdemos\_gray(i, j) & (\text{if } f\sigma(i, j)) \geq Iest - d \\ f\sigma(i, j) & (\text{if } f\sigma(i, j)) < Iest - d \end{cases} \qquad \text{formula 7}$$

Note that the merge processing unit 9 may be configured to set, as the signal "fmerge" indicating the luminance values of pixels of the "palm region" after being merged, a smaller value of the minimum value of the signal "fdemos_gray" indicating the luminance values of pixels after the grayscale conversion process has been executed and the minimum value of the signal "fσ" indicating the luminance values of pixels after the convolution operation between "f(i,j)" and the "Gaussian function g(i,j)" has been performed, in accordance with the definition represented by the following formula 8.

$$fmerge := \min(fdemos\_gray, f\sigma) \qquad \text{formula 8}$$

Next, the luminance unevenness correction unit 10 executes a correction process for the signal indicating the luminance values of pixels of the "palm region" merged in S6 so that the unevenness of the luminance values of the pixels of the "palm region" merged in S6 can be removed (S7). For example, the luminance unevenness correction unit 10 executes, in accordance with the definition represented by the following formula 9, a luminance unevenness correction process for the signal "fmerge" indicating the luminance values of pixels of the "palm region" merged in S6, and outputs a result of the process "fresult". It is assumed that a "divisor" is obtained in accordance with the definition represented by the following formula 10. "0<c≤1" is also assumed. Moreover, the luminance unevenness correction process of S7 may be omitted, and the luminance value "fmerge(i,j)" of pixels of the "palm region" merged in S6 may be output from the image processing apparatus 1.

$$fresult := \frac{fmerge}{\left(\frac{Iest}{divisor}\right)^c} \qquad \text{formula 9}$$

$$divisor := \max(i, j) \in ROI\{Iest(i, j)\} \qquad \text{formula 10}$$

Then, the biometric authentication device 3 executes a biometric authentication process by extracting the shapes of veins or the like as biological information from the image output from the luminance unevenness correction unit 10 or the merge processing unit 9, and by determining whether the extracted biological information and biological information preregistered in a storage unit match.

As described above, in the image processing apparatus 1 according to the embodiment, after low-frequency components including biological information of a subject are separated from an input image and the demosaicking process is executed for the image from which the low-frequency components have been separated, a result of the demosaicking process and the separated low-frequency components are merged. The image after being merged includes the low-frequency components even after the demosaicking process has been executed. Therefore, the biological information of a subject can be extracted with high accuracy from the image after being merged. Thus, in the image processing apparatus 1 according to the embodiment, the image process is executed for an image obtained by the general-purpose image pickup device 2, making it possible to stop hindering the extraction of biological information from the image after the image process has been executed.

Additionally, in the image processing apparatus 1 according to the embodiment, when a signal after the demosaicking process and a low-frequency component are merged, "fσ(I, m)" in which a sampling noise is reduced is used as the low-frequency component. Thus, the shapes of veins as biological information in which an SN ratio is reduced can be extracted with high accuracy from an image for which the image process has been executed by the image processing apparatus 1.

Additionally, with the image processing apparatus 1 according to the embodiment, the above described effect can be achieved even though a visible cut filter is used in the image acquisition unit 11 and a color correlation of an image output from the image acquisition unit 11 is relatively low.

Furthermore, with the image processing apparatus 1 according to the embodiment, unevenness of luminance values of pixels of a merged "palm region" is suppressed by the luminance unevenness correction unit 10. Accordingly, for example, the dynamic range of a filter included in the biometric authentication device 3 can be reduced.

FIG. 12 illustrates an image processing apparatus according to a different embodiment. The same components as those illustrated in FIG. 1 are denoted with the same reference numerals, and descriptions of the components are omitted.

The image processing apparatus 12 illustrated in FIG. 12 executes an image process such as a denoising process or the like for an image picked up by the image pickup device 2, and outputs the image to the biometric authentication device 3. The image processing apparatus 12 includes the region identification unit 4, the padding processing unit 5, the palm luminance estimation unit 6 (separation unit), the surface reflected component enhancement unit 7 (separation unit), a denoising processing unit 13, the merge processing unit 9 and the luminance unevenness correction unit 10.

Figure 13:
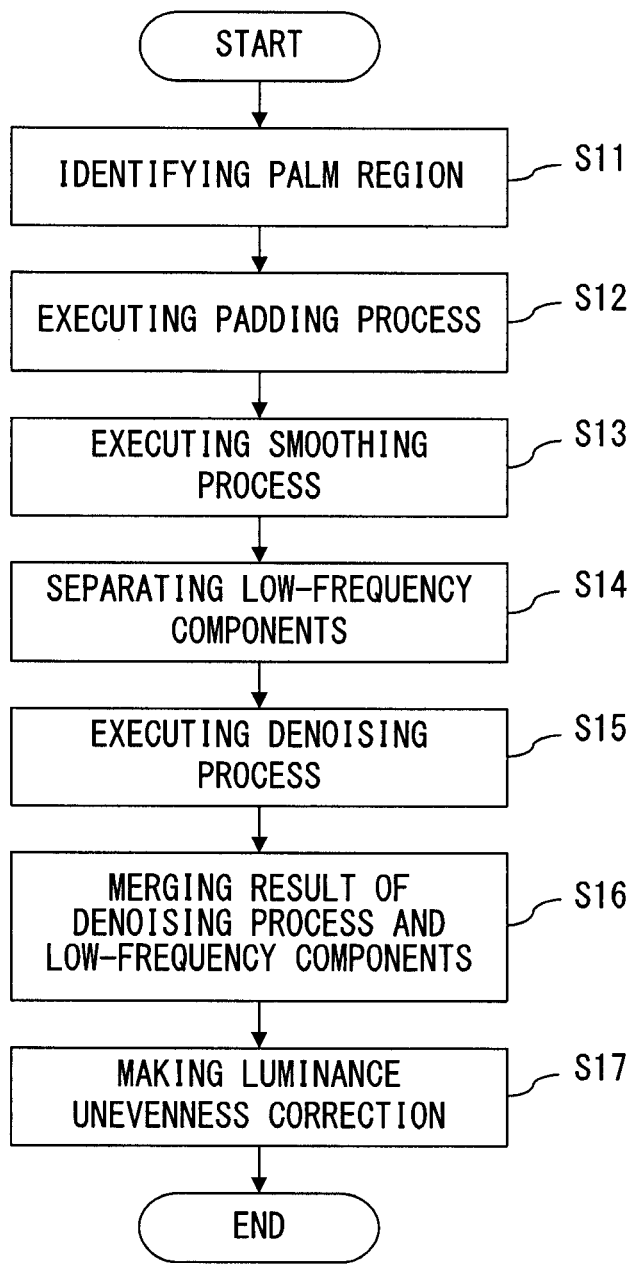
FIG. 13 is a flowchart illustrating operations of the image processing apparatus.

FIG. 13 is a flowchart illustrating operations of the image processing apparatus 12. Operations (S11 to S14, S16 and S17) other than the denoising process of S15 illustrated in FIG. 13 are the same as those (S1 to S4, S6 and S7) other than the demosaicking process of S5 illustrated in FIG. 2.

When an image obtained by the image acquisition unit 11 is input, the region identification unit 4 initially identifies a "palm region", which is a region equivalent to the palm of a subject in the image (S11).

Next, the padding processing unit 5 executes a padding process by setting luminance values of corresponding pixels among pixels of the image input in S11 as luminance values of pixels of the "palm region", and by setting an average value of luminance values set for the pixels of the "palm region" as luminance values of pixels in a region other than the "palm region" (S12).

Next, the palm luminance estimation unit 6 estimates a signal indicating the luminance values of pixels of the "palm region", in which high-frequency components (a signal indicating a luminance value that significantly changes, such as a luminance value indicating light reflected on the surface of the palm, or the like) and low-frequency components (a signal indicating a luminance value that moderately changes, such as a luminance value indicating light reflected on a vein) are reduced, by executing the smoothing process for the signal indicating the luminance values of pixels of the "palm region" set in S12 (S13).

Then, the surface reflected component enhancement unit 7 separates low-frequency components from the signal indicating the luminance values of pixels of the "palm region" set in S12 by using the signal indicating the luminance values of pixels for which the smoothing process has been executed in S13 (S14).

Next, the denoising processing unit 13 executes a denoising process for the signal indicating the luminance values of pixels of the "palm region" from which the low-frequency components have been separated in S14 (S15).

FIG. 14 illustrates an example of an observation model of a noise image.

It is assumed that a noise η additively acts on an original image f (the signal indicating the luminance values of pixels of the "palm region" from which the low-frequency components have been separated in S14 of FIG. 13) through a noise giving process step, and that a noise image F=f+η is observed by a physical observation system (observation). Here, it is assumed that the noise is additively given to the original image f for ease of explanation. The denoising process is a process for obtaining an estimation result f' of the original image f when it is assumed that F is given based on the above assumption.

Meanwhile, FIG. 15 illustrates an example of an observation model of a noise image related to the demosaicking process. Here, for the sake of explanation, the demosaicking process is described by taking, as an example, an RGB color image. However, a multi-channel image (one channel or more image) is similarly processed.

Assume that an original color image input f=(fr, fg, fb) is obtained. With a method typified by a Bayer pattern, these images are rearranged as one image (arrangement) in accordance with a particular arrangement method. After the images are rearranged, a noise η derived from an optics system acts on the image. Moreover, when images of channels are generated from this one image, an error ζ in a calculation of an image interpolation or the like is added. By observing these results (observation), a noise color image F=(Fr, Fg, Fb) is obtained. The demosaicking process is a process for obtaining an estimation result f' (f'r, f'g, f'b) of the original color image f=(fr, fg, fb) when it is assumed that F=(Fr, Fg, Fb) is given based on the above assumption.

From a viewpoint of solving an inverse problem of a noise giving process step, it can be said that the demosaicking process signifies a denoising process, which is a special case of a mosaicking process.

In contrast, mainly from a viewpoint of a process, arrangement/rearrangement may be an identity transformation in a special case where the number of channels is 1 in the demosaicking process, and there is no error of an interpolation. Namely, the demosaicking process in this case is a general denoising process.

Next, in the flowchart of FIG. 13, the merge processing unit 9 merges the signal indicating the luminance values of pixels of the "palm region" for which the denoising process has been executed in S15 and the low-frequency components separated in S14 (S16).

Then, the luminance unevenness correction unit 10 executes a correction process for the signal indicating the luminance values of pixels of the "palm region" merged in S16 so that the unevenness of the luminance values of pixels of the "palm region" merged in S16 can be removed (S17).

Next, the biometric authentication device 3 executes a biometric authentication process by extracting the shapes of veins or the like as biological information from an image output from the luminance unevenness correction unit 10 or the merge processing unit 9, and by determining whether the extracted biological information and biological information prestored in a storage unit match.

As described above, also in the image processing apparatus 12 according to the different embodiment, after low-frequency components including biological information of a subject are separated from an input image and the denoising process is executed for the image after being separated, a result of the denoising process and the separated low-frequency components are merged. The image after being merged includes the low-frequency information even after the denoising process has been executed. Therefore, the biological information of the subject can be extracted with a high accuracy from the image after being merged. Thus, in the image processing apparatus 12 according to this embodiment, the image process is executed for the image obtained by the general-purpose image pickup device 2, making it possible to stop hindering the extraction of biological information from the image after the image process has been executed.

Figure 16:
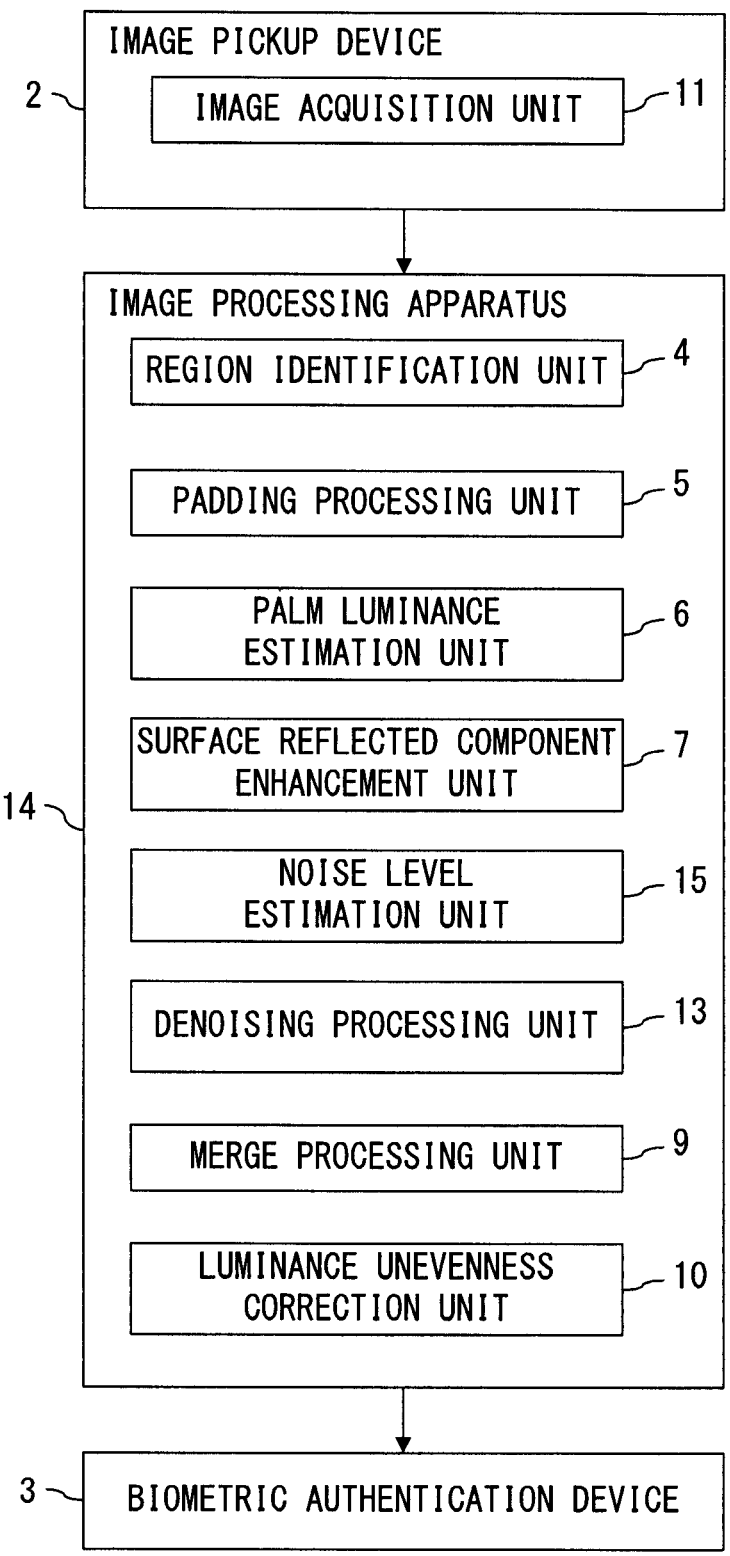
FIG. 16 illustrates an image processing apparatus according a further different embodiment.

FIG. 16 illustrates an image processing apparatus according to a further different embodiment. The same components as those illustrated in FIG. 12 are denoted with the same reference numerals, and descriptions of the components are omitted.

The image processing apparatus 14 illustrated in FIG. 16 executes an image process such as a denoising process or the like for an image picked up by the image pickup device 2, and outputs the image to the biometric authentication device 3. The image processing apparatus 14 includes the region identification unit 4, the padding processing unit 5, the palm luminance estimation unit 6 (separation unit), the surface reflected component enhancement unit 7 (separation unit), a noise level estimation unit 15, the denoising processing unit 13, the merge processing unit 9 (merging unit) and the luminance unevenness correction unit 10.

Figure 17:
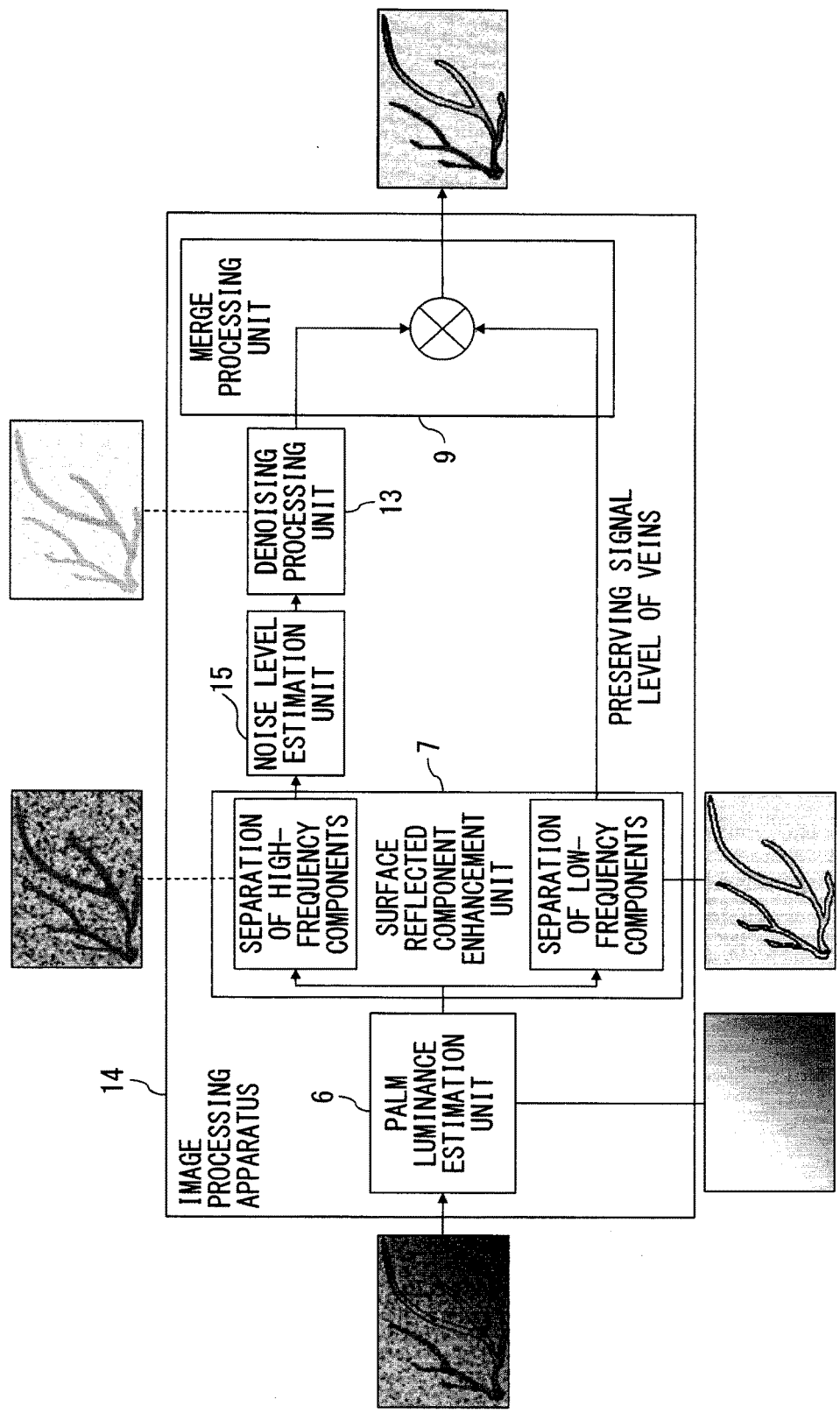
FIG. 17 schematically illustrates the image processing apparatus.

FIG. 17 schematically illustrates the image processing apparatus 14 depicted in FIG. 16. In FIG. 17, the region identification unit 4, the padding processing unit 5 and the luminance unevenness correction unit 10 are not illustrated.

As illustrated in FIGS. 16 and 17, in the image processing apparatus 14, the denoising process is executed for the signal indicating the luminance values of pixels of the "palm region" from which low-frequency components have been separated by the surface reflected component enhancement unit 7 after a noise level is estimated.

FIG. 18 is a flowchart illustrating operations of the image processing apparatus 14. In the operations illustrated in FIG. 18, operations (S21 to S24, S26 to S28) other than an estimation of a noise level of S25 are the same as the operations (S11 to S17) illustrated in FIG. 13.

When an image obtained by the image acquisition unit 11 is input, the region identification unit 4 initially identifies a "palm region", which is a region equivalent to the palm of a subject in the image (S21).

Next, the padding processing unit 5 executes a padding process by setting luminance values of corresponding pixels among pixels of the image input in S21 as luminance values of pixels of the "palm region", and by setting an average value of luminance values set for the pixels of the "palm region" as luminance values of pixels of a region other than the "palm region" (S22).

Next, the palm luminance estimation unit 6 estimates the signal indicating the luminance values of pixels of the "palm region", in which high-frequency components (a signal indicating a luminance value that significantly changes, such as a luminance value indicating light reflected on the surface of the palm) and low-frequency components (a signal indicating a luminance value that moderately changes, such as a luminance value indicating light reflected on a vein) are reduced, by executing the smoothing process for the signal indicating the luminance values of pixels of the "palm region" set in S22 (S23).

Next, the surface reflected component enhancement unit 7 separates the low-frequency components from the signal indicating the luminance values of pixels of the "palm region" set in S22 by using the signal indicating the luminance values of pixels for which the smoothing process has been executed in S23 (S24).

Then, the noise level estimation unit 15 estimates a noise level for the signal indicating the luminance values of pixels of the "palm region" from which the low-frequency components have been separated in S24 (S25).

Figure 19:
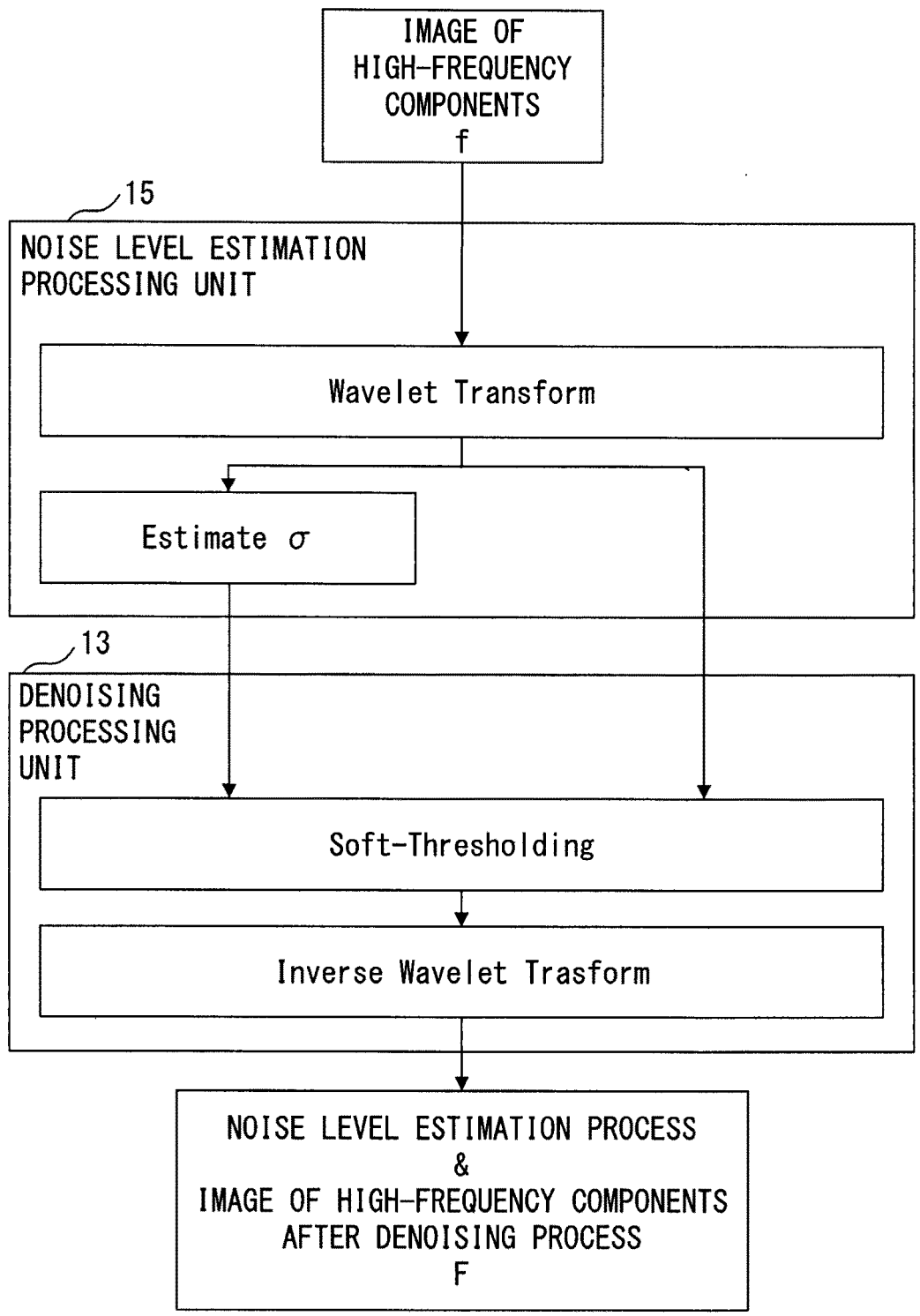
FIG. 19 illustrates an example of a noise level estimation unit and a denoising processing unit.

Next, the denoising processing unit 13 executes, by using the noise level estimated in S25, the denoising process for the signal indicating the luminance values of pixels of the "palm region" from which the low-frequency components have been separated in S24, namely, the signal indicating the luminance values of pixels of the "palm region" of high-frequency components (S26). As the estimation of the noise level and the denoising process, for example, a process using a Wavelet transform is conceivable, as illustrated in FIG. 19. See "S. D. Ruikar, D. D. Doye, Wavelet Based Image Denoising Technique, IJACSA, vol. 2, no. 3, March 2011".

Next, in the flowchart of FIG. 18, the merge processing unit 9 merges the signal indicating the luminance values of pixels of the "palm region" for which the denoising process has been executed in S26 and the low-frequency components separated in S24 (S27).

Then, the luminance unevenness correction unit 10 executes the correction process for the signal indicating the luminance values of pixels of the "palm region" merged in S27 so that the unevenness of luminance values of pixels of the "palm region" merged in S27 can be removed (S28).

Then, the biometric authentication device 3 executes the biometric authentication process by extracting the shapes of veins as biological information from the image output from the luminance unevenness correction unit 10 or the merge processing unit 9, and by determining whether the extracted biological information and biological information prestored in a storage unit match.

As described above, also in the image processing apparatus 14 according to a different embodiment, after low-frequency components including biological information of a subject are separated from an input image and the denoising process is executed for the image after being separated, a result of the denoising process and the separated low-frequency components are merged. The image after being merged includes the low-frequency components even after the denoising process has been executed. Therefore, the biological information of the subject can be extracted with high accuracy from the image after being merged. Thus, the image process is executed for the image obtained by the general-purpose image pickup device 2 in the image processing apparatus 14 according to the different embodiment, making it possible to stop hindering the extraction of biological information from the image after the image process has been executed.

Additionally, in the image processing apparatus 14 according to the different embodiment, the "palm region" is identified by the region identification unit 4, and the estimation of the noise level and the denoising process are executed for the "palm region". Accordingly, a noise estimation and a noise removal can be robustly performed even when an image is shot under various environments.

FIG. 20 illustrates an image processing apparatus according to a further different embodiment. The same components as those illustrated in FIG. 1 or 16 are denoted with the same reference numerals, and descriptions of the components are omitted.

The image processing apparatus 16 illustrated in FIG. 20 executes an image process such as a demosaicking process for an image picked up by the image pickup device 2, and outputs the image to the biometric authentication device 3. The image processing apparatus 16 includes the region identification unit 4, the padding processing unit 5, the palm luminance estimation unit 6 (separation unit), the surface reflected component enhancement unit 7 (separation unit), the noise level estimation unit 15, the demosaicking processing unit 8, the merge processing unit 9 and the luminance unevenness correction unit 10.

Figure 21:
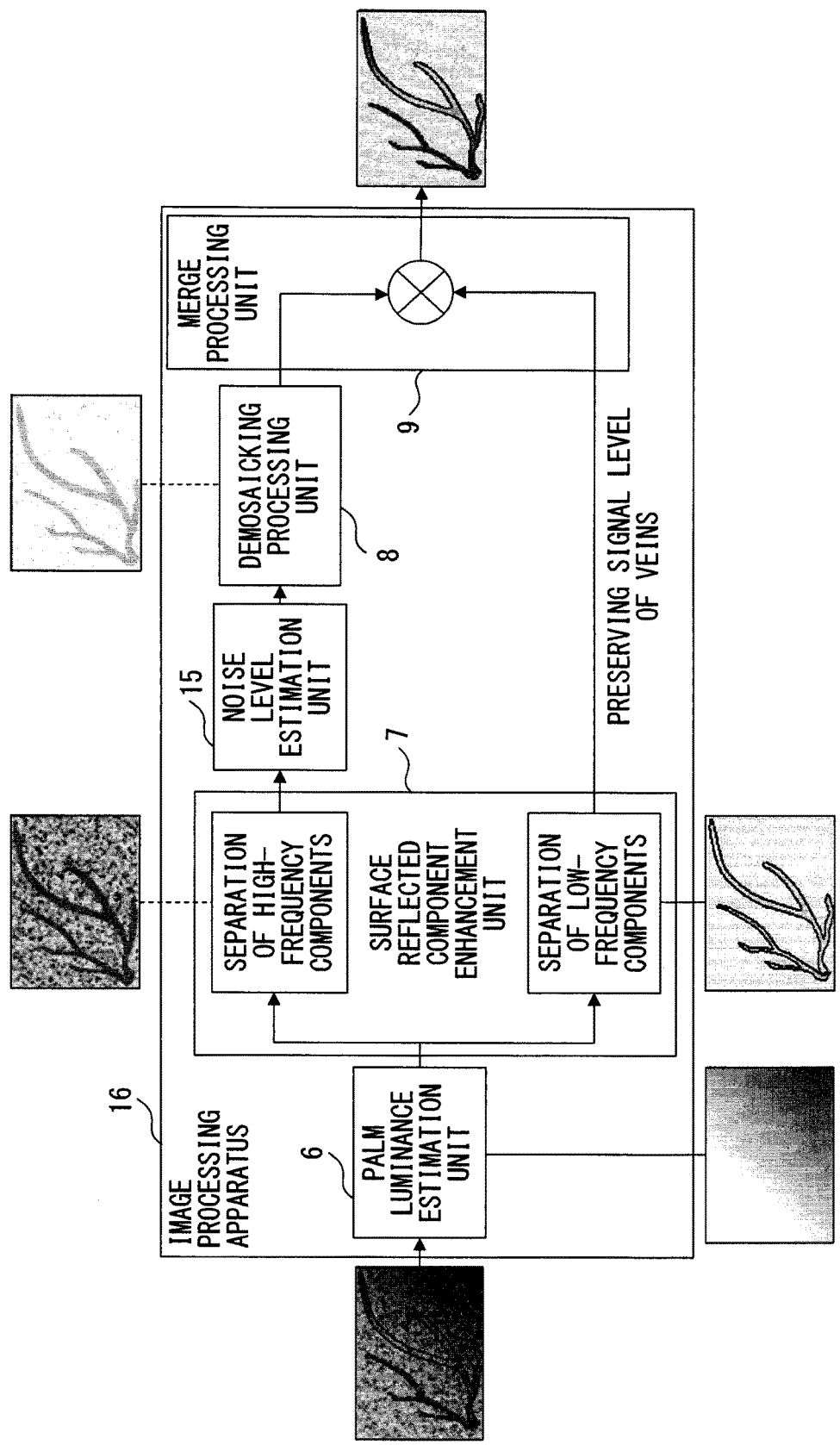
FIG. 21 schematically illustrates the image processing apparatus.

FIG. 21 schematically illustrates the image processing apparatus 16 depicted in FIG. 20. In FIG. 21, the region identification unit 4, the padding processing unit 5 and the luminance unevenness correction unit 10 are not illustrated.

As illustrated in FIGS. 20 and 21, in the image processing apparatus 16, after the noise level estimation is performed for a signal indicating luminance values of pixels of the "palm region" from which a low-frequency component has been separated by the surface reflected component enhancement unit 7, the demosaicking process is executed.

Figure 22:
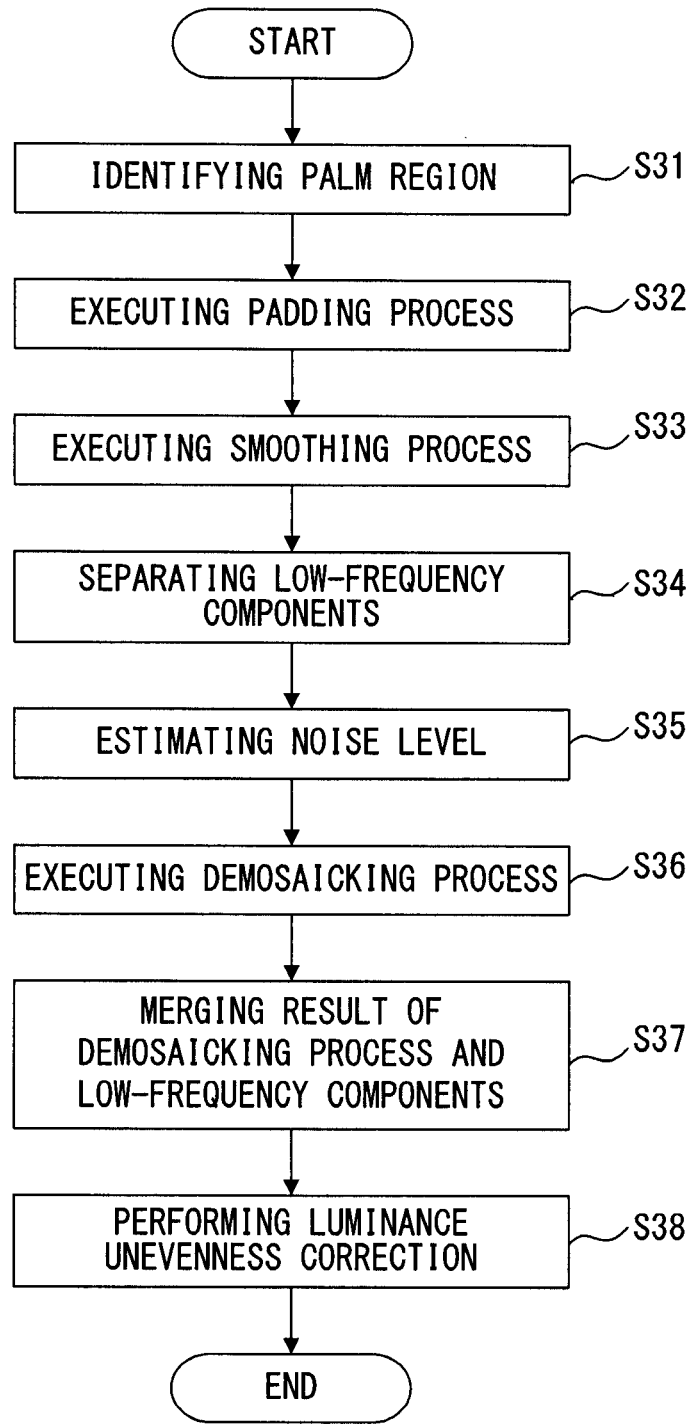
FIG. 22 is a flowchart illustrating operations of the image processing apparatus.

FIG. 22 is a flowchart illustrating operations of the image processing apparatus 16. In the operations illustrated in FIG. 22, S31 to S34 are the same as S1 to S4 of FIG. 2, S11 to S14 of FIG. 13, or S21 to S24 of FIG. 18, S35 is the same as S25 of FIG. 18, and S36 to S38 are the same as S5 to S7 of FIG. 2.

When an image obtained by the image acquisition unit 11 is input, the region identification unit 4 initially identifies the "palm region", which is a region equivalent to the palm of a subject in the image (S31).

Next, the padding processing unit 5 executes the padding process by setting luminance values of corresponding pixels among pixels of the image input in S31 as luminance values of pixels of the "palm region", and by setting an average value of the luminance values set for the pixels of the "palm region" as luminance values of pixels of a region other than the "palm region" (S32).

Then, the palm luminance estimation unit 6 estimates a signal indicating the luminance values of pixels of the "palm region", in which a high-frequency component (for example, a signal indicating a luminance value that significantly changes, such as a luminance value indicating light reflected on the surface of the palm) and a low-frequency component (for example, a signal indicating a luminance value that moderately changes, such as a luminance value indicating light reflected on a vein) are reduced, by executing the smoothing process for the signal indicating the luminance values of pixels of the "palm region" set in S32 (S33).

Next, the surface reflected component enhancement unit 7 separates the low-frequency component from the signal indicating the luminance values of pixels of the "palm region" set in S32 by using the signal indicating the luminance values of pixels for which the smoothing process has been executed in S33 (S34).

Next, the noise level estimation unit 15 estimates a noise level for the signal indicating the luminance values of pixels of the "palm region" from which the low-frequency component has been separated in S34 (S35).

Then, the demosaicking processing unit 8 executes a demosaicking process for the signal indicating the luminance values of pixels of the "palm region" from which the low-frequency component has been separated in S34, namely, the signal indicating the luminance values of pixels of the "palm region" of high-frequency components, by using the noise level estimated in S35, (S36).

Next, the merge processing unit 9 merges the signal indicating the luminance values of pixels of the "palm region" for which the demosaicking process has been executed in S36 and the low-frequency component separated in S34 (S37).

Then, the luminance unevenness correction unit 10 executes a correction process for the signal indicating the luminance values of pixels of the "palm region" merged in S37 so that the unevenness of luminance values of pixels of the "palm region" merged in S37 can be removed (S38).

Next, the biometric authentication device 3 executes a biometric authentication process by extracting the shapes of veins or the like as biological information from the image output from the luminance unevenness correction unit 10 or the merge processing unit 9, and by determining whether the extracted biological information and biological information prestored in a storage unit match.

As described above, also in the image processing apparatus 16 according to the further different embodiment, after a low-frequency component including biological information of a subject is separated from an input image and the demosaicking process is executed for the image after being separated, a result of the process and the separated low-frequency component are merged. The image after being merged includes the low-frequency component even after the demosaicking process has been executed. Therefore, the biological information of the subject can be extracted with high accuracy from the image after being merged. Thus, in the image processing apparatus 16 according to the further different embodiment, the image process is executed for an image obtained by the general-purpose image pickup device 2, making it possible to stop hindering the extraction of biological information from an image after the image process has been executed.

Additionally, in the image processing apparatus 16 according to the further different embodiment, the "palm region" is identified by the region identification unit 4, and a noise level estimation and the demosaicking process are executed in the "palm region". Therefore, the noise estimation and the noise removal can be robustly performed even when an image is shot under various environments.

FIG. 23 illustrates an example of hardware that configures the image processing apparatus 1.

As illustrated in FIG. 23, the hardware that configures the image processing apparatus 1, 12, 14 or 16 includes a control unit 1201, a storage unit 1202, a recording medium reading device 1203, an input/output interface 1204 and a communication interface 1205. These components are interconnected by a bus 1206. The hardware that configures the image processing apparatus 1, 12, 14 or 16 may be implemented by using a cloud technology or the like.

As the control unit 1201, for example, a Central Processing Unit (CPU), a multi-core CPU, a programmable device (a Field Programmable Gate Array (FPGA), and a Programmable Logic Device (PLD) or the like) are conceivable to be available. The control unit 1201 is equivalent to the region identification unit 4, the padding processing unit 5, the palm luminance estimation unit 6, the surface reflected component enhancement unit 7, the demosaicking processing unit 8, the merge processing unit 9 and the luminance unevenness correction unit 10, which are illustrated in FIGS. 1 and 20, the denoising processing unit 13 illustrated in FIG. 12, and the noise level estimation unit 15 illustrated in FIGS. 16 and 20.

As the storage unit 1202, for example, a memory such as a Read Only Memory (ROM), a Random Access Memory (RAM) or the like, a hard disk and the like are conceivable. The storage unit 1202 may be used as a working area at the time of execution. Moreover, another storage unit may be provided outside the information processing apparatus 1, 12, 14 or 16.

The recording medium reading device 1203 reads or writes data from or to a recording medium 1207 in accordance with control of the control unit 1201. Moreover, an insertable/removable recording medium 1207 is a non-transitory computer-readable recording medium. As the recording medium 1207, for example, a magnetic recording device, an optical disc, a magneto-optical recording medium, a semiconductor memory and the like are conceivable. As the magnetic recording device, for example, a hard disk device (HDD) and the like are conceivable. As the optical disc, for example, a Digital Versatile Disc (DVD), a DVD-RAM, a Compact Disc-Read Only Memory (CD-ROM), a CD-R (Recordable)/RW (ReWritable) and the like are conceivable. As the magneto-optical recording medium, for example, a Magneto-Optical disk (MO) and the like are conceivable. The non-transitory recording media also includes the storage unit 1202.

To the input/output interface 1204, the input/output unit 1208 is connected. The input/output interface 1204 transmits information input by a user from the input/output unit 1208 to the control unit 1201 via the bus 1206. Moreover, the input/output interface 1204 transmits information transmitted from the control unit 1201 to the input/output unit 1208 via the bus 1206.

As the input/output unit 1208, for example, a keyboard, a pointing device (a mouse or the like), a touch panel, a Cathode Ray Tube (CRT) display, a printer and the like are conceivable.

The communication interface 1205 is an interface for making a Local Area Network (LAN) connection, and an Internet connection. Moreover, the communication interface 1205 may be used as an interface for making a LAN connection with another computer, an Internet connection, or a wireless connection when needed.

A computer having such hardware is used whereby there are various types of process functions that the image processing apparatus 1, 12, 14 or 16 executes. In this case, the computer executes a program that describes contents of the various process functions executed by the image processing apparatus 1, whereby the above described process functions (such as the region identification unit 4, the padding processing unit 5, the palm luminance estimation unit 6, the surface reflected component enhancement unit 7, the demosaicking processing unit 8, the merge processing unit 9, and the luminance unevenness correction unit 10) are implemented on the computer. The program that describes the contents of the various types of process functions can be stored in the storage unit 1202 or on the recording medium 1207.

When the program is distributed, for example, the recording medium 1207, such as a DVD, a CD-ROM or the like, on which the program is recorded is marketed. Moreover, the program can be recorded in a recording device of a server computer, and can be also transferred from the server computer to another computer via a network.

The computer that executes the program stores, for example, the program recorded on the recording medium 1207, or the program transferred from the server computer in the storage unit 1202. Then, the computer reads the program from the storage unit 1202, and executes the processes according to the program. The computer can also read the program directly from the recording medium 1207, and can execute the processes according to the program. Moreover, the computer can execute a process according to a received program each time the program is transferred from the server computer.

The above described embodiments have been described by taking, as an example, the image processing apparatus that performs authentication by using the veins of the palm. However, the embodiments are not limited to the implementations using the veins of the palm. Any portion of a living body may be used as long as a feature can be detected from the portion.

For example, the portion of the living body from which a feature is detected is not limited to the veins. A blood vessel image of the living body, a pattern of the living body, fingerprints or palm prints of the living body, the sole of foot, fingers of the hand or the foot, an arch of the hand or the foot, the wrist, the arm or the like may be available.

When the veins are used for authentication, the portion of the living body from which a feature is detected may be a portion where the veins are observable.

If the portion of the living body from which a feature is detected is a portion having a feature with which biological information is identifiable, it is more advantageous. For example, if the portion is the palm, the face or the like, it is identifiable from an obtained image.

Additionally, the above described embodiments can be variously changed within a scope that does not depart from the gist of the embodiments. Moreover, a person skilled in the art can diversely modify and change the above described embodiments, and the embodiments are not limited to the abovementioned precise configurations and application examples.

According to the present invention, it becomes possible to stop hindering the extraction of biological information from an image obtained by a general-purpose image pickup device.

All examples and connectional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An image processing apparatus, comprising:
a computer having hardware and units programmed to perform process functions, the units including,
a separation unit that separates low-frequency components from a signal indicating luminance values of pixels of an input image;
a demosaicking processing unit that executes a demosaicking process for the signal from which the low-frequency components have been separated; and
a merging unit that generates an image by merging the signal after the demosaicking process and the low-frequency components; wherein
a noise level estimation unit estimates a noise level for the signal from which the low-frequency components have been separated;
a correction unit corrects luminance values of pixels of the image generated by the merging unit so that unevenness of the luminance values of pixels of the image generated by the merging unit can be removed, and
the demosaicking processing unit executes the demosaicking process by using a result of an estimation of the noise level.

2. An image processing method, comprising:
separating, by a computer, low-frequency components from a signal indicating luminance values of pixels of an input image;
executing, by the computer, a demosaicking process for the signal from which the low-frequency components have been separated; and
generating, by the computer, an image by merging the signal after the demosaicking process and the low-frequency components;
the method further comprising:
estimating, by the computer, a noise level for the signal from which the low-frequency components have been separated;
executing, by the computer, a demosaicking process by using a result of an estimation of the noise level; and
correcting, by the computer, luminance values of pixels of the generated image so that unevenness of the luminance values of pixels of the generated image can be removed.

3. A non-transitory computer-readable recording medium having stored there in a program for causing a computer to execute a digital signature process comprising:
separating low-frequency components from a signal indicating luminance values of pixels of an input image;
executing a demosaicking process for the signal from which the low-frequency components have been separated; and
generating an image by merging the signal after the demosaicking process and the low-frequency components,
the digital signature process further comprising:
estimating a noise level for the signal from which the low-frequency components has been separated, and executing a demosaicking process by using a result of an estimation of the noise level; and
correcting luminance values of pixels of the generated image so that unevenness of the luminance values of pixels of the generated image can be removed.

* * * * *